(12) United States Patent
Butler

(10) Patent No.: US 7,981,099 B2
(45) Date of Patent: Jul. 19, 2011

(54) DEODORIZING GAS FILTER ASSEMBLY FOR A BODY WASTE COLLECTION POUCH, AND METHOD OF MAKING

(75) Inventor: Donncha R. Butler, County Mayo (IE)

(73) Assignee: Hollister Incorporated, Libertyville, IL (US)

( * ) Notice: Subject to any disclaimer, the term of this patent is extended or adjusted under 35 U.S.C. 154(b) by 569 days.

(21) Appl. No.: 12/170,552

(22) Filed: Jul. 10, 2008

(65) Prior Publication Data
US 2010/0010460 A1    Jan. 14, 2010

(51) Int. Cl.
*A61F 5/44*    (2006.01)
*B01D 53/22*    (2006.01)

(52) U.S. Cl. ........ 604/333; 604/327; 604/328; 604/329; 604/330; 604/331; 604/332; 604/334; 604/335; 604/336; 604/337; 604/338; 604/339; 604/340; 604/341; 604/342; 604/343; 604/345; 604/346; 604/347; 604/348; 604/349; 96/9; 96/11; 96/134; 96/136; 96/137; 96/139; 96/152; 96/189; 96/190; 96/361; 96/362; 96/364; 96/367

(58) Field of Classification Search .................. 604/333, 604/327–332, 334–349; 96/9, 11, 134, 136, 96/137, 139, 152, 189–190, 361–362, 364, 96/367
See application file for complete search history.

(56) References Cited

U.S. PATENT DOCUMENTS

| | | | |
|---|---|---|---|
| 3,759,260 A | 9/1973 | Nolan et al. | |
| 4,274,848 A * | 6/1981 | La Gro | ................................ 96/6 |
| 4,449,970 A * | 5/1984 | Bevan et al. | .................. 604/333 |
| 4,460,392 A | 7/1984 | Poulsen et al. | |
| 4,778,601 A | 10/1988 | Lopatin et al. | |
| 5,306,264 A * | 4/1994 | Ferguson et al. | .............. 604/333 |
| 5,370,638 A | 12/1994 | Keyes | |
| 5,468,235 A * | 11/1995 | La Gro | .......................... 604/333 |
| 5,733,271 A * | 3/1998 | Bjørn | ............................. 604/333 |

(Continued)

FOREIGN PATENT DOCUMENTS

| | | |
|---|---|---|
| EP | 1 514 528 | 3/2005 |
| GB | 2 059 797 | 4/1981 |
| GB | 2 276 324 | 9/1994 |

OTHER PUBLICATIONS

International Search Report and Written Opinion for Application No. PCT/US2009/033860, dated Apr. 3, 2009.

*Primary Examiner* — Melanie J Hand
*Assistant Examiner* — Ginger T Chapman
(74) *Attorney, Agent, or Firm* — Marshall, Gerstein & Borun LLP

(57) ABSTRACT

A high performance flatus gas filter assembly, and a body waste collection pouch with which it may be used, along with a method for making such an assembly, are disclosed. The assembly includes a filter pad having first and second layers of deodorizing filter media with an imperforate gas and odor barrier layer sandwiched therebetween for blocking the direct flow of gases between the opposing inner faces of the filter layers. An envelope of liquid and gas impermeable material defines a chamber for enclosing the pad. The envelope has walls with first and second openings communicating with central portions of the first and second filter layers, and defines a peripheral space about the pad to permit the outward flow of flatus gases from the peripheral edge surface of one of the filter layers inwardly into the peripheral edge surface of the other of the filter layers.

32 Claims, 3 Drawing Sheets

U.S. PATENT DOCUMENTS

| | | | |
|---|---|---|---|
| 6,135,986 A * | 10/2000 | Leisner et al. | 604/322 |
| 6,506,184 B1 | 1/2003 | Villefrance | |
| 6,824,595 B2 * | 11/2004 | Ueki et al. | 96/134 |
| 7,326,190 B2 | 2/2008 | Botten | |
| 7,341,578 B2 * | 3/2008 | Bulow et al. | 604/333 |
| 2006/0271002 A1 | 11/2006 | Botten | |

* cited by examiner

FIG. 1
FIG. 2
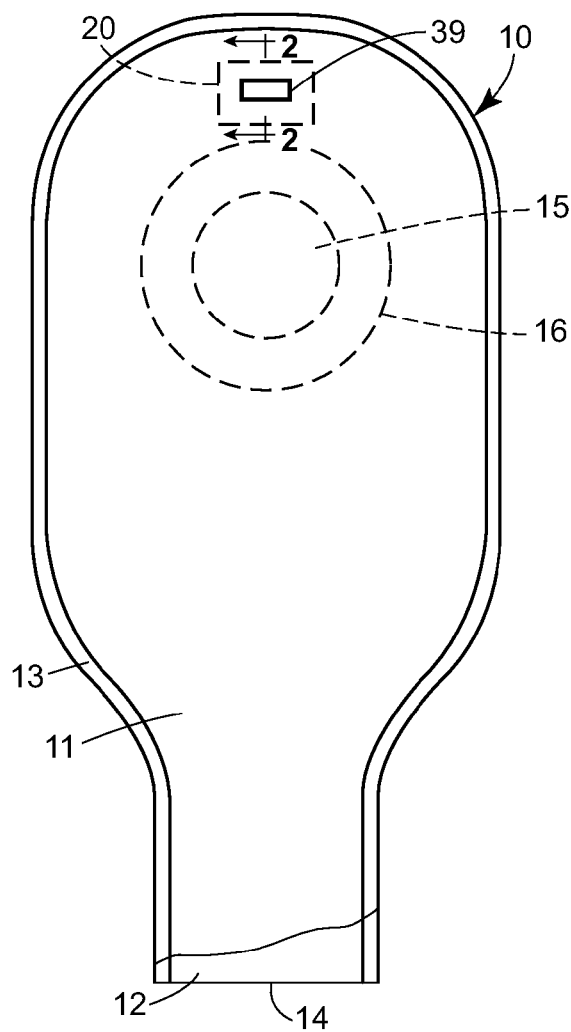
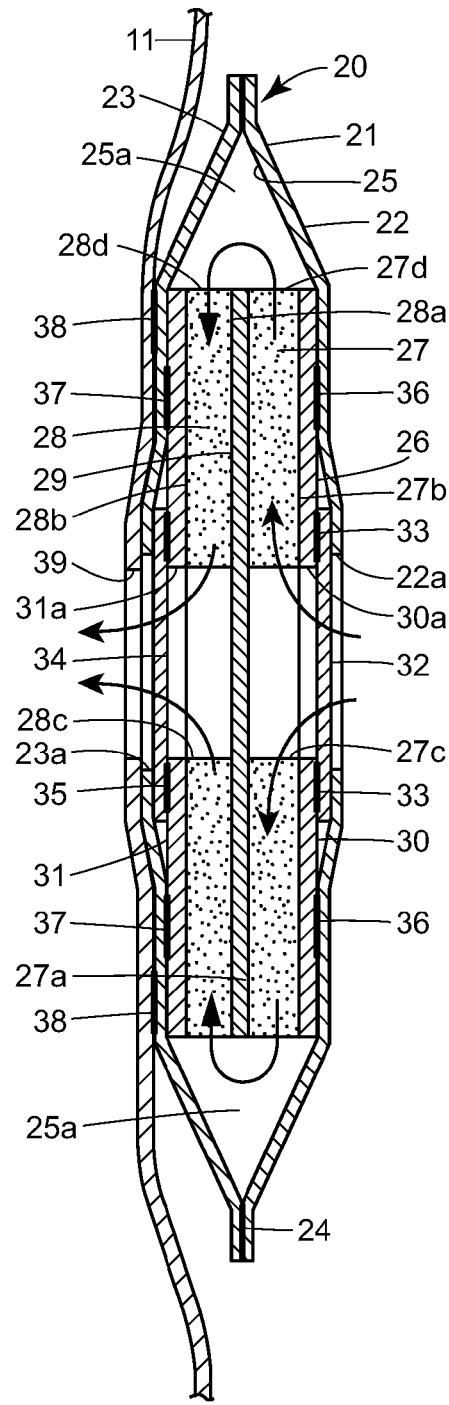

DEODORIZING GAS FILTER ASSEMBLY FOR A BODY WASTE COLLECTION POUCH, AND METHOD OF MAKING

BACKGROUND

Botten patent U.S. Pat. No. 7,326,190 discloses a high performance deodorizing gas filter assembly for body waste collection pouches in which a radial flow filter pad is located in an envelope having first and second openings laterally spaced from each other. In a preferred embodiment, the pad is oblong or elongate and has a first passage communicating with the envelope's first opening and a second passage spaced laterally from the first passage and communicating with the envelope's second opening. Flatus gases may therefore enter the first passage through the first opening, flow in generally radial directions through and about the filter to the second passage, and exit from the envelope through the second opening. Hydrophobic microporous membranes extend over each of the openings to prevent liquids from entering the envelope and impairing operation of the filter while at the same time allowing gases to flow therethrough. While such an arrangement achieves impressive filtering performance in terms of gas transmission rate and deodorizing efficiency, such achievements are obtained by reason of a radial flow filter assembly of relative large area or outline.

Villefrance patent U.S. Pat. No. 6,506,184 is also directed to the use of radial flow filters for body waste collection pouches and shows that they may be located inside, outside, or both inside and outside such pouches (see FIGS. 2, 4 and 6, respectively). Other patents disclosing radial flow filters are Keyes U.S. Pat. No. 5,370,638, Poulsen et al U.S. Pat. No. 4,460,392 and Nolan et al U.S. Pat. No. 3,759,260.

SUMMARY

An important aspect of this disclosure is to provide a high performance radial flow filter assembly that may equal or even exceed the flow transmission characteristics and filtering efficiency of the Botten filter assembly but has a relatively small footprint, that is, it occupies smaller area. The assembly may include a filter pad having first and second filter layers of deodorizing filter media that are coextensive, superposed, and have planar inner and outer faces and exposed peripheral edge surfaces. An imperforate gas and odor barrier layer, which may include one or more imperforate films, is sandwiched between the first and second filter layers for blocking the direct flow of gases between the opposed inner faces of those filter layers.

The assembly may include an envelope formed of liquid and gas impermeable material that defines a chamber enclosing the pad. The opposing walls of the envelope may have openings communicating with central portions of the first and second filter layers, respectively, and may be sealed directly or indirectly to the outer faces of the pad's filter layers about such openings. The envelope provides peripheral spacing about the pad to permit the flow of flatus gases from the peripheral edge surface of one of the filter layers to that of the other filter layer. Thus, flatus gases may enter the envelope through one of the axially-aligned envelope openings, pass into one of the filter layers through the central portion of the outer face thereof, flow radially outwardly through the one filter layer to enter the peripheral space about the pad, and then into the peripheral edge surface of the other of the filter layers, flowing radially inwardly through the other filter layer and exiting the assembly through the other of the envelope openings.

At least one of the envelope openings, and preferably both of them, have gas permeable, but generally liquid impermeable, or at least liquid resistant, hydrophobic membranes of microporous material extending thereacross to prevent liquids and solids from entering the assembly and obstructing the gas filtering action of the pad. Both membranes, or at least the one facing the interior of the body waste collection pouch, should additionally be formed of a material that is also oleophobic.

In a preferred embodiment, the filter pad includes not only the two layers of filter media on opposite sides of an imperforate gas and odor barrier layer, but also skin layers or films of gas impermeable material sealed to the outer faces of the filter layers. Both skin layers or films are provided with openings aligned with the openings of the envelope.

In one embodiment, each of the filter layers of the pad may have a centrally located passage to promote conversion between axial flow of gas entering and leaving the assembly through the envelope openings and radial inward and outward flow of gas through the pad itself.

The filter assembly may be located either externally or internally of a waste collection pouch, the latter being preferred. In either case, a vent opening may be provided in a wall of the pouch for the outward flow of deodorized gas away from the assembly (if internally located) or toward the assembly (if externally located). In one embodiment, the assembly may be in the form of a complete subassembly in which both walls of the envelope are parts of that subassembly or, alternatively, in another embodiment, the filter assembly may be integrated with the pouch so one of the pouch walls also functions as a wall of the envelope.

The disclosure also includes a method of making a deodorizing gas filter assembly. In that method, a generally rectangular blank or sheet of a filter laminate serves as the starting material. The sheet comprises a porous core layer of activated carbon interposed between first and second outer or skin layers of liquid and gas impermeable film. The sheet has a transverse midline extending between a pair of sections (preferably rectangular) on each side thereof. A pair of apertures or openings are formed (or preformed) in the first skin layer at central locations in each of the sections. Gas permeable but liquid resistant microporous membranes are secured over each of the apertures. In production, the sheet is cut along the transverse midline through at least the first skin layer and the core layer, and the two sections are then arranged, preferably by folding along the transverse midline, so that the sectional components of the second skin layer face each other to form a filter sandwich in which the two components of the second skin layer are interposed between the core layer components of the sandwich. The filter sandwich is then enclosed in a gas-impermeable envelope, such envelope having side walls with openings in register with (and sealed about) the two apertures in the folded components of the first skin layer. Within the envelope, peripheral spacing is provided about the filter sandwich for the flow of gases from one core layer component to the other.

BRIEF DESCRIPTION OF THE DRAWINGS

In the drawings, the parts are not shown to scale. Thicknesses have been increased in some instances for clarity of illustration and to facilitate description of the structure, its functioning, and its method of manufacture.

FIG. 1 is a front elevational view of an ostomy pouch equipped with a high performance deodorizing filter assembly.

FIG. 2 is an enlarged schematic sectional view taken along line 2-2 of FIG. 1.

DETAILED DESCRIPTION

Figure 3:
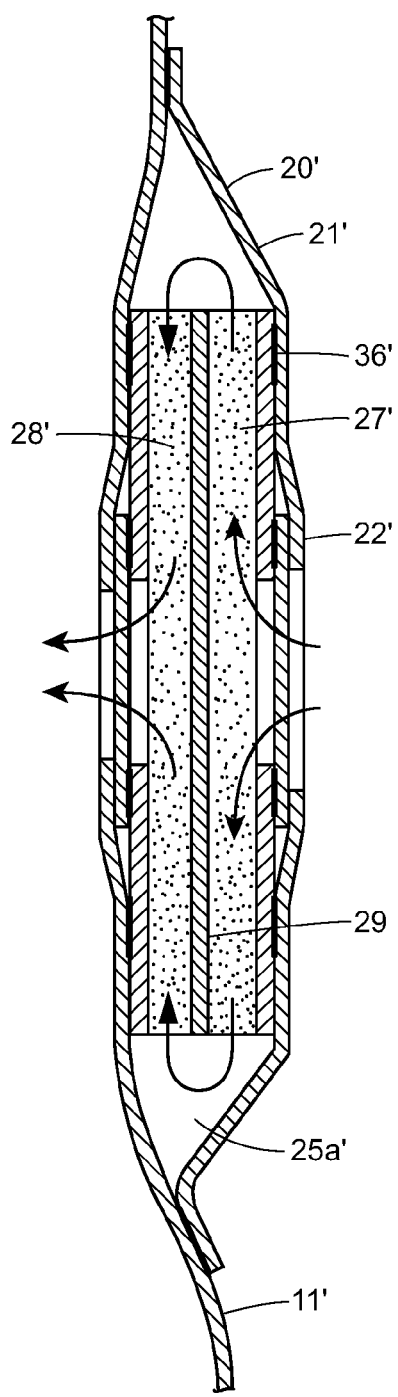
FIG. 3 is an enlarged sectional view similar to FIG. 2 but depicting a second embodiment of the disclosure.

FIG. 1 illustrates an ostomy pouch 10 having front and rear walls 11 and 12 joined along their edges by heat sealing 13 or by any other suitable means. The pouch shown is a drainable pouch with a drain opening 14 that may be closed by folding and/or clamping by any of a variety of known closure techniques. Alternatively, the drain opening may be omitted and the pouch may be of the non-drainable variety. Rear wall 12 has a stoma-receiving opening 15 surrounded by attachment means 16. In the illustration, the pouch is one component of a so-called two-piece appliance and its attachment means takes the form of a coupling ring which mechanically and releasably engages the coupling ring component of a faceplate (not shown) adhesively securable to a wearer, all of which is well known in the art. Alternatively, the attachment means 16 may take the form or an adhesive ring or patch designed to adhesively engage the peristomal skin surfaces of a wearer (i.e., a one-piece appliance) or the smooth surface of a faceplate which in turn is adhesively secured to the wearer (an adhesive two-piece appliance).

Filter assembly 20 is most clearly shown in FIG. 2. The filter assembly 20 includes an envelope 21 having first and second walls 22 and 23 of flexible plastic film joined together along their edges by heat seal 24 to define a filter chamber 25. Within the chamber is a generally flat multilayer filter pad 26 having first and second filter layers 27 and 28 of deodorizing filter media. The layers 27 and 28 of filter media have planar faces, and may be manufactured using any of a variety of known techniques for making odor-absorbing ostomy pouch filters. One example is a standard paper-making technique with fibers, usually polymeric, that are coated with finely-divided activated carbon using a suitable binder such as a conventional binder used in paper-making procedures. In general, the carbon should be finely-divided with the maximum size thereof being no greater than 100 microns, and with a size distribution in which more than one-half of the particles are less than 50 microns in size. Alternatively, the filter layers 27 and 28 may be composed of carbonized viscous rayon textile as disclosed in U.S. Pat. No. 6,506,184, the disclosure of which is incorporated by reference herein. For purposes of this disclosure, any porous odor-absorbing filter material known for use in deodorizing flatus gases vented from an ostomy pouch is believed suitable.

The pad 26 also includes an imperforate gas and odor barrier layer 29 sandwiched between filter layers 27 and 28 and sealed to the opposing inner faces 27a and 28a of the filter layers 27 an 28, thereby blocking the axial flow of gases from one filter layer to the other. While the barrier layer is shown as being a thin film of occlusive material, it may, as described hereinafter, include two or more contiguous films sealed to the respective opposing surfaces of the filter layers.

The outer faces 27b and 28b of the filter layers 27 and 28 are also preferably covered by gas-impermeable films 30 and 31 sealed thereto. All of the films 29-31 may be composed of polyethylene or other polyolefin, or any other thin, flexible, preferably heat-sealable polymeric film known to have gas and odor barrier properties. Films 30 and 31 may alternatively take the form of gas and odor impermeable coatings applied to the outer faces 27b and 28b of filter layers 27 and 28. Further, in some instances the films or coatings 30 and 31 may even be omitted and their functions performed by walls 22 and 23 of the envelope 21, as where such wall are sealed by adhesive or other suitable means directly to the outer faces 27b and 28b of the filter layers 27 and 28.

All of the layers 27-31 may be coextensive in their outer dimensions and may be superposed or stacked as shown. In the embodiment of FIG. 2, the filter layers 27 and 28 have central openings or passages 27c and 28c extending axially therethrough, and the films 30 and 31 have openings 30a and 31a in register with such passages. The film openings 30a and 31a and passages 30a and 31a are aligned, concentric with and preferably follow the peripheral contour of the filter pad 26; hence, if the filter pad 26 is circular in outline, the openings and passages would also be circular, whereas if the filter pad 26 is rectangular in shape (as shown), the film openings 30a and 31a and passages 30a and 31a would also preferably be of rectangular shape, insuring that the distances of radial flow through the filter layers along vertical and horizontal axes of the surfaces of the filter pad 26 are essentially equal.

A microporous membrane 32 of gas-transmissible but liquid (water) impermeable, or at least liquid resistant, material covers the central portion of one outer surface of the filter pad 26, extending over opening 30a of film 30 and passage 27c of filter layer 27 and being sealed to the film 30 about its opening 30a by heat seal 33. In the embodiment of FIG. 2, a similar membrane 34 covers the central portion of the opposite outer surface of the filter pad 26, extending over opening 31a of film 31 and passage 28a of filter layer 28. Membrane 32 protects the filter media from exposure to the liquid and solid contents of the pouch and for that reason should be oleophobic as well as hydrophobic. The other membrane 34 might in some instances be omitted but its presence is important and preferred because it protects the filter media from exposure to water from an external source such as, for example, a shower. While membrane 34 may be oleophobic as well as hydrophobic, and may be of the same composition as that of membrane 32, it may, if desired, be only hydrophobic instead of both hydrophobic and oleophobic.

A number of materials suitable for the membranes are commercially available, one being "Gore-Tex", a microporous polytetrafluoroethylene membrane marketed by W. L. Gore & Associates, Newark, Del. While different porosities for such a membrane may be suitable, it is preferred that the membrane have a pore size allowing passage through the membrane only of particles have a maximum dimension smaller than 3 microns, and more preferably 2 microns or less. Another material suitable for use as a microporous hydrophobic and oleophobic membrane is available from Millipore Corporation, Bedford, Mass., and is disclosed in U.S. Pat. No. 4,778,601, incorporated herein by reference. Such a membrane is understood to be composed of microporous ultra high molecular weight polyethylene.

It is of particular importance that the filter pad 26 be disposed in envelope 21 with a peripheral space 25a extending about the peripheral edge surfaces 27d and 28d of the filter layers of the filter pad 26. Also, the walls 22 and 23 of the envelope 21 may be sealed, as by heat seals 36 and 37, or by other suitable means, to the outer surfaces of the filter pad 26. In FIG. 2, seal 36 is between envelope wall 22 and film 30, and seal 37 is between envelope wall 23 and film 31, both seals surrounding the openings or apertures 30a and 31a of the respective films. Finally, the walls 22 and 23 of the envelope 21 are provided with openings 22a and 23a, respectively, which may be aligned and communicate with the openings or apertures 30a and 31a of films 30 and 31 that may be covered by microporous membranes 32 and 34.

The filter assembly 20 so far described is a subassembly that may be secured by heat seal 38 to wall 11 of the pouch with the opening 23a of the envelope 21 aligned with a vent opening 39 formed in the pouch wall.

In operation, flatus gases in the pouch 10 flow into the filter assembly 20 through envelope opening 22a and through microporous membrane 32 and then radially outwardly through the first filter layer 27 into the peripheral space 25a, following the flow path represented by the arrows in FIG. 2. The radial flow then reverses, with the gases flowing inwardly through filter layer 28 and exiting the filter assembly 20 and pouch 10 through membrane 34, envelope opening 23, and pouch vent opening 39. Throughout such operation, barrier layer 29 blocks direct axial flow between filter layers 27 and 28. The result is a high performance filter assembly that has a notably small footprint but a relatively long and effective filtering pathway for deodorizing flatus gases.

The embodiment of FIG. 3 is similar to that already described except for two main differences: Filter assembly 20' utilizes a portion of wall 11' of the pouch as one of the walls of the envelope 21', and the central passages 27c and 28c of the filter layers of the previous embodiment are omitted in filter layers 27' and 28'. In structure, function and operation, the two embodiments are otherwise equivalent. It is to be understood, however, that central passages similar to passages 27c and 28c of the first embodiment may also if desired be provided in the embodiment of FIG. 3.

Figure 4:
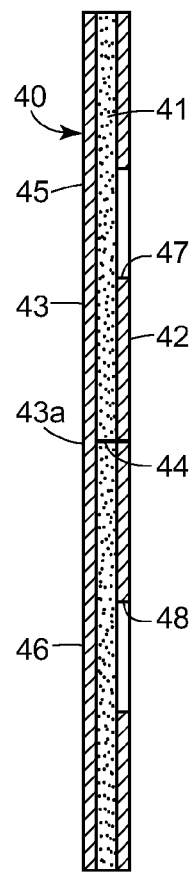
FIGS. 4-9 are a series of sectional views illustrating a sequence of steps in a method of making the pouch with a deodorizing filter constituting the second embodiment of the disclosure.
Figure 5:
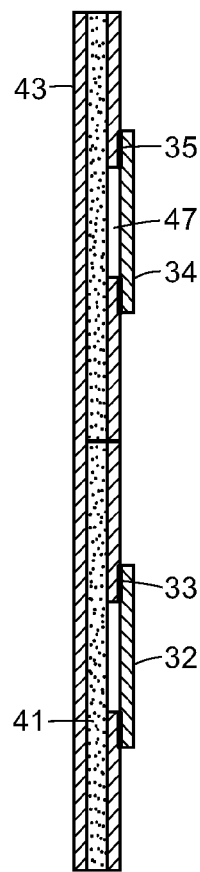
Figure 6:
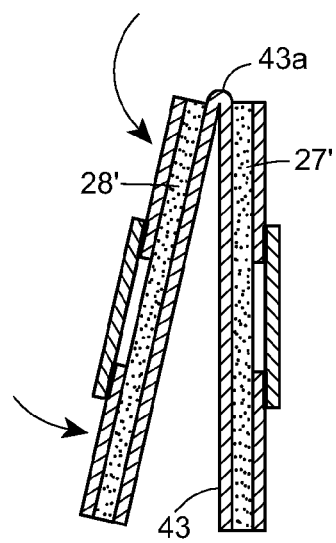

FIGS. 4 through 9 schematically depict a method for making the pouch and flatus gas filter assembly of FIG. 3. The item shown in FIG. 4 is a laminated sheet 40 having a porous core layer 41 of activated carbon and gas-deodorizing filter media disposed between first and second skin layers 42 and 43 of flexible, liquid and gas impermeable film. A straight cut 44 is made along the transverse midline of the sheet. While that cut might extend completely through the sheet, separating it into two disconnected sections, it is preferred that the cut extend only through the first skin layer 42 and through core layer 41, with skin layer 43 providing a living hinge 43a along the transverse midline. Thus, the straight cut 44 partially separates the sheet into two sections 45 and 46 of identical shape and size, with the living hinge 43a then allowing the sections to be folded into contiguous superposed relation as shown in FIG. 6.

Sheet 40 is preferably rectangular in shape, so that each of the sections 45 and 46 on opposite sides of the transverse midline is also of rectangular shape. While a rectangular configuration is considered advantageous, other shapes are possible. For example, the sheet might be formed as two generally circular, oval, hexagonal, or octagonal sections that then remain tangentially connected following a cutting operation by reason of an integral hinge provided by uncut film 43.

Referring to FIG. 4, the first skin layer or film 42 has a pair of apertures 47 and 48 cut or milled therein, each being centrally located in one of the sections 45 and 46. The apertures might be formed prior to lamination of the layers of the sheet, but it is believed preferable to do so later, recognizing that even if some of the material of the core layer 41 is simultaneously removed at the sites of the apertures, the resulting assembly will still be operative (its operation might even be enhanced in view of the passages 27a and 28a found in the embodiment of FIG. 2) as long as the second skin layer 43 remains imperforate.

In the step depicted in FIG. 5, microporous membranes 32 and 34 are secured by heat seals 33 and 35 to the first skin layer or film 42 over the apertures 48 and 47, respectively.

Figure 7:
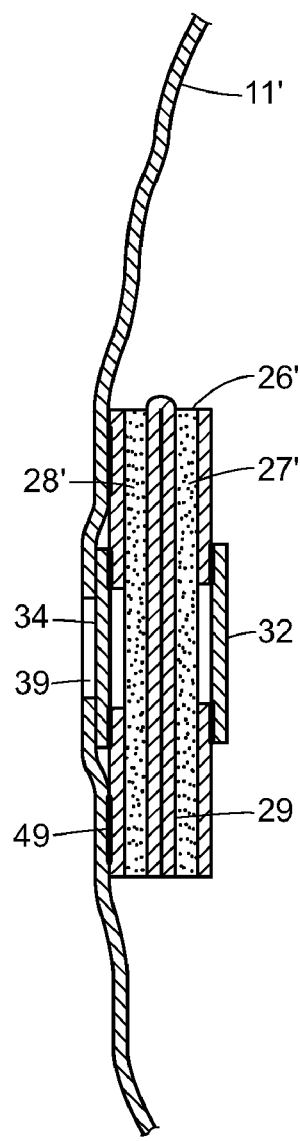
Figure 8:
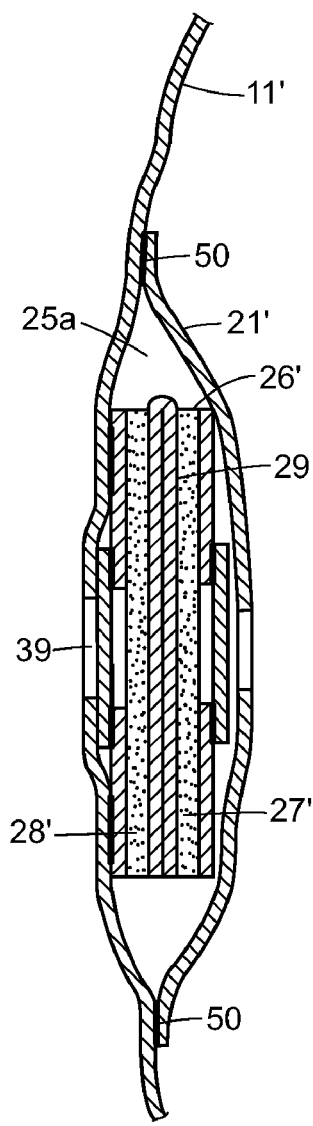

Thereafter, the sheet is folded along living hinge 43a, bringing the two sectional components of skin layer 43 into facing relation (FIG. 6). Those sectional components of skin layer 43, taken together, constitute the imperforate gas and odor barrier layer 29 of the filter assembly previously described, with such barrier layer sandwiched between the two sections of the core layer 41 which then constitutes the filter layers 27' and 28' (FIG. 7). While if desired the two components of the barrier layer 29 might be adhesively tacked together, if desired, it is unnecessary that their opposing surfaces be sealed together in their entireties.

Figure 9:
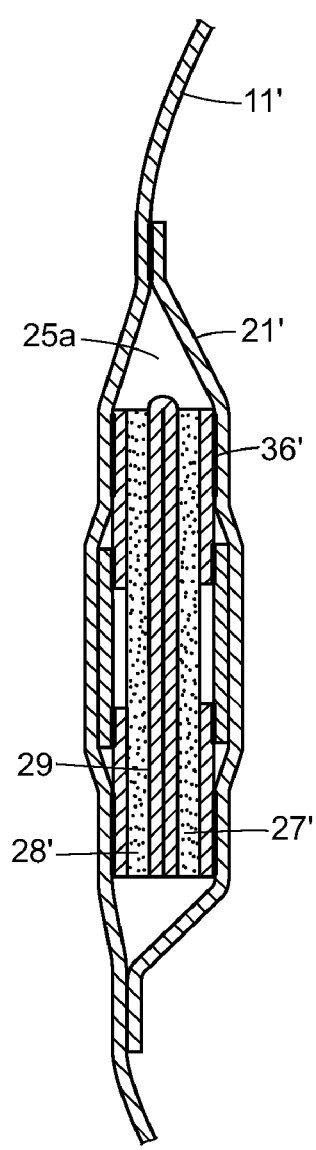

In the concluding operations, the filter pad 26' may be secured to wall 11' of the pouch by perimetric heat seal 49, with the microporous membranes 32 and 34 and the openings they cover, being aligned with vent opening 39 of the pouch (FIG. 7); a second wall 22' of the envelope 21' (the pouch wall 11' being the other envelope wall) may be joined by heat seal 50 to pouch wall 11' at a distance outboard of the peripheral edge surfaces of the pad 26' so as to form a peripheral air space 25a thereabout (FIG. 8); and the second wall 22' of the envelope 21' is heat sealed at 36' to film 30 of the filter pad (FIG. 9).

The invention claimed is:

1. A deodorizing flatus gas filter assembly for body waste collection pouches, comprising a filter pad having first and second filter layers of deodorizing filter media;
   said layers being coextensive and superposed, with said filter layers having planar outer faces, opposed planar inner faces, and exposed peripheral edge surfaces;
   and an imperforate gas and odor barrier layer sandwiched between said first and second filter layers for blocking the direct flow of gases between said opposed inner faces;
   said assembly also including an envelope formed of liquid and gas impermeable material defining a chamber enclosing said pad;
   said envelope having walls with first and second openings communicating with central portions of said first and second filter layers, respectively;
   said pad having an outer surface sealed to one of the walls of the envelope;
   said envelope defining a peripheral space about said pad to permit the flow of flatus gases from a peripheral edge surface of one of said filter layers to the peripheral edge surface of the other said filter layers;
   whereby, flatus gases may enter said envelope through one of said envelope openings, enter one of said filter layers through said central portion of said outer face thereof, flow radially outwardly through said one filter layer to enter said peripheral space and then into the peripheral edge surface of the other of said filter layers to flow radially inwardly through said other of said filter layers and exit the assembly through the other of said envelope openings.

2. The filter assembly of claim 1 in which said outer faces of said first and second filter layers are each covered by a gas-impermeable film sealed thereto, each said film having a film opening in register with one of said envelope openings.

3. The filter assembly of claim 2 in which each of said films is sealed to a wall of said envelope about said registered openings of said film and envelope.

4. The filter assembly of claims 1, 2 or 3 in which one of said walls of said envelope comprises the wall of a body waste collection pouch.

5. The filter assembly of claim 4 in which said assembly is located internally of said pouch.

6. The filter assembly of claim 4 in which said assembly is located externally of said pouch.

7. The filter assembly of claims 1, 2 or 3 in which said imperforate gas and odor barrier layer comprises at least one barrier film.

8. The filter assembly of claim 7 in which said gas and odor barrier layer comprises two barrier films, one of which is sealed to the entire inner face of said first filter layer and the other of which is sealed to the entire inner face of said second filter layer.

9. The filter assembly of claims 1, 2 or 3 in which at least one of said envelope openings has a gas-permeable liquid-resistant membrane formed of hydrophobic microporous material extending thereacross.

10. The filter assembly of claim 9 in which both of said envelope openings have gas-permeable liquid-resistant microporous membranes of hydrophobic material extending thereacross.

11. The filter assembly of claim 10 in which at least one of said membranes is formed of a material that is also oleophobic.

12. The filter assembly of claim 11 in which said assembly is located in a body waste collection pouch; said microporous membrane formed of a material that is also oleophobic being located within the interior of said pouch and said envelope opening across which said membrane extends being a flatus gas inlet opening.

13. The filter assembly of claims 1, 2 or 3 in which said layers of said filter media have aligned central passages extending axially therethrough.

14. A body waste collection pouch having front and rear walls joined together along their peripheral edges;
    said rear wall having a waste-receiving opening externally surrounded by attachment means for securing said pouch to a wearer;
    a deodorizing flatus gas filter assembly within said pouch comprising a filter pad having first and second filter layer of deodorizing filter media;
    said layers being coextensive and superposed, with said filter layers having planar outer faces, opposed planar inner faces, and exposed peripheral edge surfaces;
    and an imperforate gas and odor barrier layer sandwiched between said first and second filter layers for blocking the direct flow of gases between said opposed inner faces;
    said assembly also including an envelope formed of liquid and gas impermeable material defining a chamber enclosing said pad within said pouch;
    said envelope having walls with first and second openings communicating with central portions of said outer faces of said first and second filter layers, respectively;
    said pad having an outer surface sealed to one of the walls of the envelope;
    said envelope defining a peripheral space about said pad to permit the flow of flatus gases from a peripheral edge surface of one of said filter layers to the peripheral edge surface of the other of said filter layers;
    said first opening of said envelope constituting a flatus gas inlet opening for said assembly and said second opening constituting an outlet opening;
    said outlet opening communicating externally of said pouch.

15. The pouch of claim 14 in which said wall of said envelope having said outlet opening comprises a wall of said pouch.

16. The pouch of claim 14 in which said wall of said envelope having said outlet opening is sealed to one of said walls of said pouch within said pouch chamber; said one wall of said pouch having a vent opening communicating with said outlet opening.

17. The pouch of claims 14, 15 or 16 in which said outer faces of said first and second filter layers are each covered by a gas-impermeable film sealed thereto, each said film having a film opening in register with one of said envelope openings.

18. The pouch of claim 17 in which each of said films is sealed to a wall of said envelope about said registered openings of said films and envelope.

19. The pouch of claims 14, 15 or 16 in which said imperforate gas and odor barrier layer comprises at least one barrier film.

20. The pouch of claim 19 in which said gas and odor barrier layer comprises two barrier films, one of which is sealed to the entire inner face of said first filter layer and the other of which is sealed to the entire inner face of said second filter layer.

21. The pouch of claims 14, 15 or 16 in which at least one of said envelope openings has a gas-permeable liquid-resistant membrane formed of hydrophobic microporous material extending thereacross.

22. The pouch of claim 21 in which both of said envelope openings has a gas-permeable liquid-resistant of hydrophobic microporous material extending thereacross.

23. The pouch of claim 22 in which at least one of said membranes is formed of a material that is also oleophobic.

24. The pouch of claims 14, 15 or 16 in which each of said layers of said filter media has a central passage extending axially therethrough.

25. A method of making a deodorizing gas filter assembly for body waste collection pouches, comprising the steps of
    forming a laminated sheet having a porous core layer of activated carbon particles disposed between first and second skin layers of liquid and gas impermeable film;
    said sheet defining in outline a pair of sections on each side of a transverse midline;
    said first skin layer having a pair of vent apertures, each located in a central portion of each said section;
    securing a gas-permeable but liquid-resistant microporous membrane over each of said vent apertures;
    cutting said sheet along said transverse midline through at least said first skin layer and through said core layer;
    then arranging said sections so that the second skin layer components of each are disposed in facing relation, thereby forming a filter sandwich with the second skin layer components of said sections located between the core layers components of said sections which in turn are covered by apertured first skin layers components of said sections;
    and then enclosing said filter sandwich in a gas-impermeable envelope having a pair of side walls with openings in register with and sealed about each of said apertures, said envelope defining a peripheral space extending about peripheral edge surfaces of the filter sandwich.

26. The method of claim 25 in which said enclosing step includes locating said envelope within a body waste collection pouch having a gas discharge opening in a wall thereof with one of said envelope openings of said envelope being aligned with a gas discharge vent opening of said pouch.

27. The method of claim 25 in which one of said walls of said envelope comprises a wall of a body waste collection pouch having a gas discharge vent opening aligned with and sealed about one of said apertures of said filter sandwich.

28. The method of claim 27 in which said enclosing step includes locating said filter sandwich within the interior of said body waste collection pouch.

29. The method of claim 25 in which said skin layers are formed of flexible polymeric film and said cutting step comprises cutting through only said first skin layer and said core layer, leaving a portion of said second skin layer along said midline as a living hinge.

30. The method of claim 29 in which said arranging step includes folding said filter sandwich at said living hinge to bring said first skin layer components of said sections into facing relation.

31. The method of claim 25 in which said enclosing step includes leaving a peripheral space within said envelope about said filter sandwich.

32. The method of claim 25 in which said sheet is generally rectangular and in which said two sections on opposite sides of said midline are each of equal area and of generally rectangular shape.

* * * * *